(12) United States Patent
Wang et al.

(10) Patent No.: US 7,761,138 B2
(45) Date of Patent: Jul. 20, 2010

(54) MRI AND X-RAY VISUALIZATION

(75) Inventors: Lixiao Wang, Long Lake, MN (US); Jan Weber, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1760 days.

(21) Appl. No.: 10/799,094

(22) Filed: Mar. 12, 2004

(65) Prior Publication Data

US 2005/0215874 A1     Sep. 29, 2005

(51) Int. Cl.
*A61M 25/00*     (2006.01)
(52) U.S. Cl. .................. 600/435; 600/407; 600/414; 600/426; 600/427; 623/1.16; 623/1.34; 623/1.42
(58) Field of Classification Search .......... 600/407, 600/414, 426, 427, 431, 420, 411; 623/1.16, 623/1.34, 1.42
See application file for complete search history.

(56) References Cited

U.S. PATENT DOCUMENTS

| | | | |
|---|---|---|---|
| 4,572,198 A | 2/1986 | Codrington | |
| 4,976,690 A | 12/1990 | Solar et al. | |
| 4,985,233 A | 1/1991 | Klaveness et al. | |
| 4,989,608 A | 2/1991 | Ratner et al. | |
| 5,154,179 A | 10/1992 | Ratner | |
| 5,270,086 A | 12/1993 | Hamlin | |
| 5,271,400 A | 12/1993 | Dumoulin et al. | |
| 5,447,156 A | 9/1995 | Dumoulin et al. | |
| 5,628,787 A | 5/1997 | Mayer | |
| 5,699,801 A | 12/1997 | Atalar et al. | |
| 5,702,682 A | 12/1997 | Thompson | |
| 5,725,570 A | 3/1998 | Heath | |
| 5,728,079 A | 3/1998 | Weber et al. | |
| 5,738,632 A | 4/1998 | Karasawa | |
| 5,744,958 A | 4/1998 | Werne | |
| 5,817,017 A | 10/1998 | Young et al. | |
| 5,908,410 A | 6/1999 | Weber et al. | |
| 5,964,705 A | 10/1999 | Truwit et al. | |
| 6,026,316 A * | 2/2000 | Kucharczyk et al. | 600/420 |
| 6,042,605 A | 3/2000 | Martin et al. | |
| 6,123,920 A | 9/2000 | Gunther et al. | |
| 6,207,134 B1 | 3/2001 | Fahlvik et al. | |
| 6,217,607 B1 | 4/2001 | Alt | |
| 6,245,104 B1 | 6/2001 | Alt | |
| 6,263,229 B1 | 7/2001 | Atalar et al. | |
| 6,272,370 B1 * | 8/2001 | Gillies et al. | 600/411 |
| 6,280,385 B1 | 8/2001 | Melzer et al. | |
| 6,334,871 B1 * | 1/2002 | Dor et al. | 623/1.34 |
| 6,340,367 B1 | 1/2002 | Stinson et al. | |
| 6,423,296 B1 | 7/2002 | Gunther et al. | |
| 6,436,056 B1 | 8/2002 | Wang et al. | |

(Continued)

OTHER PUBLICATIONS

International Search Report mailed Aug. 9, 2005, received in International Application No. PCT/US2005/007644.

(Continued)

*Primary Examiner*—Long V Le
*Assistant Examiner*—Ellsworth Weatherby
(74) *Attorney, Agent, or Firm*—Crompton, Seager & Tufte, LLC

(57) ABSTRACT

Markers that are visible under magnetic resonance imaging (MRI) and fluoroscopy and related medical devices are disclosed.

62 Claims, 5 Drawing Sheets

U.S. PATENT DOCUMENTS

| | | |
|---|---|---|
| 6,463,317 B1 | 10/2002 | Kucharczyk et al. |
| 6,545,097 B2 | 4/2003 | Pinchuk et al. |
| 6,574,497 B1 | 6/2003 | Pacetti |
| 6,585,755 B2 | 7/2003 | Jackson et al. |
| 6,589,286 B1 | 7/2003 | Litner |
| 6,612,998 B2 | 9/2003 | Gosiengfiao et al. |
| 6,884,234 B2* | 4/2005 | Aita et al. ............... 604/103.01 |
| 2002/0165523 A1 | 11/2002 | Chin et al. |
| 2003/0004563 A1 | 1/2003 | Jackson et al. |
| 2003/0099764 A1 | 5/2003 | Li et al. |
| 2003/0100830 A1 | 5/2003 | Zhong et al. |
| 2003/0163117 A1* | 8/2003 | Ishii ............................ 604/523 |
| 2004/0186377 A1* | 9/2004 | Zhong et al. ................. 600/431 |
| 2004/0193140 A1* | 9/2004 | Griffin et al. ................. 604/524 |
| 2005/0124976 A1* | 6/2005 | Devens et al. ................ 604/523 |
| 2005/0131522 A1* | 6/2005 | Stinson et al. .............. 623/1.15 |
| 2005/0215885 A1* | 9/2005 | Lee et al. ..................... 600/420 |
| 2005/0255317 A1* | 11/2005 | Bavaro et al. ................ 428/375 |
| 2006/0111646 A1* | 5/2006 | Gellman et al. .............. 600/562 |
| 2007/0093142 A1* | 4/2007 | MacDonald et al. ........ 439/676 |

OTHER PUBLICATIONS

Albert C. Chin et al., "Multilayer Balloon Catheter", U.S. Appl. No. 10/351,695, filed Jan. 27, 2003.

Eckhard Alt, "Stent with Outermost Ceramic-Like Layer", U.S. Appl. No. 10/651,562, filed Aug. 29, 2003.

* cited by examiner

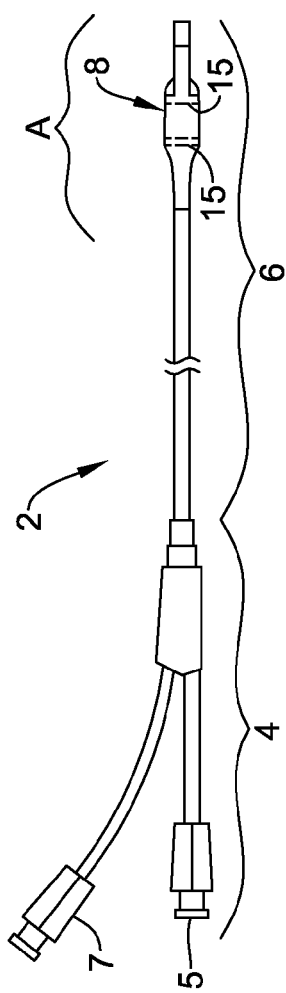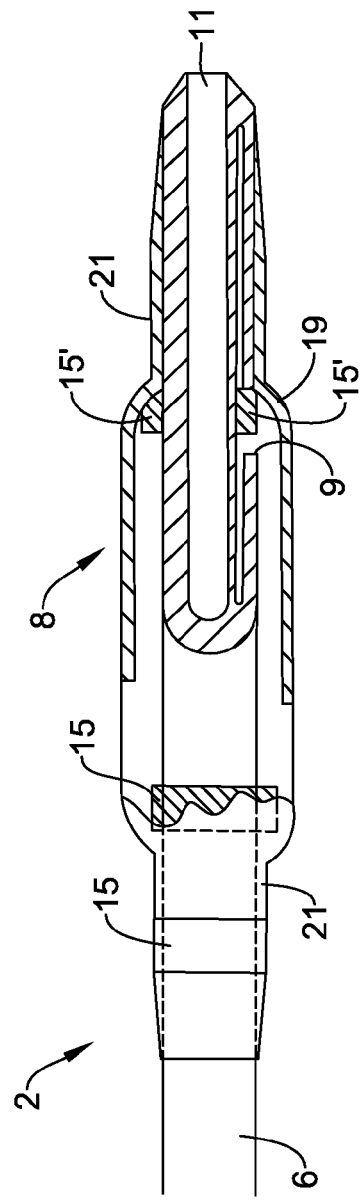

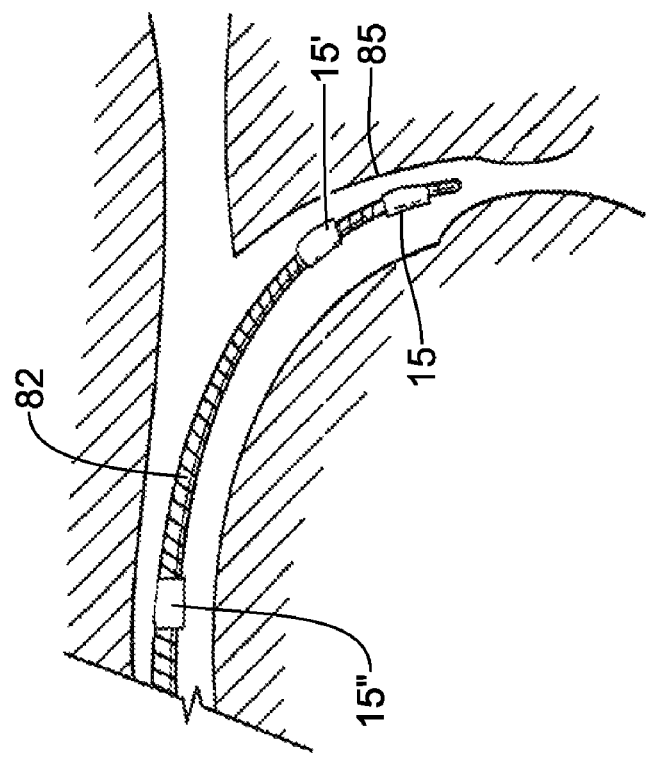
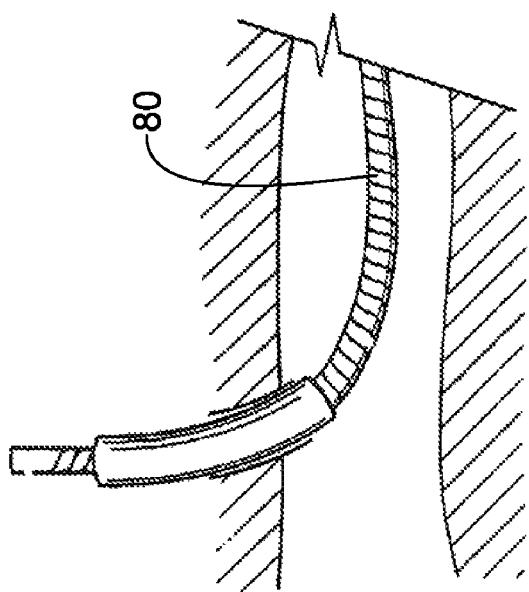
Figure 6

MRI AND X-RAY VISUALIZATION

TECHNICAL FIELD

This invention relates to MRI and X-ray visualization.

BACKGROUND

Medical professionals, such as physicians, use visualization techniques to help guide placement or activation of implantable medical devices, such as catheters, stents, embolization coils, etc., within a patient's body. Fluoroscopy is a common visualization technique in which X rays directed towards the patient's body interact with materials to produce an image. Materials that are highly radiopaque absorb X rays to create contrast within the image, and thus are visible. MRI is another visualization technique used by medical professionals. These images are produced from complex interactions between nuclear spin and electromagnetic fields.

SUMMARY

In an aspect, the invention features a marking system that includes a fluoroscopic imaging enhancement material and an MRI enhancement material.

In an aspect, the invention features a marking system for use with a medical device to mark a region thereof. The system includes a body that is attachable to the medical device. The body includes a fluoroscopic imaging enhancement material and an MRI enhancement material. The fluoroscopic imaging enhancement material is provided in a first layer and the MRI enhancement material is provided in a second layer. The first and second layers are concentric with each other and are bonded.

In an aspect, the invention features a marking system for use with a medical device to mark a region thereof. The marking system includes a body with three or more layers. One or more of the three or more layers of the marking system includes a fluoroscopic imaging enhancement material and/or a MRI enhancement material.

In an aspect, the invention features a method of attaching a marker to a medical device. The method includes positioning at least one marker at a location along the medical device. The marker includes a fluoroscopic imaging enhancement material and an MRI enhancing material. The marker is secured at the location.

In an aspect, the invention features a medical device, including a body formed of a biocompatible material (e.g. of polymer) and a marker secured to the body. The marker includes a fluoroscopic imaging enhancement material and an MRI enhancing material.

In aspects, the invention features methods of making markers and marking systems and using the markers and marking systems in medical treatments.

Embodiments may include one or more of the following. The marker is secured by friction. The marker is secured by adhesive. The marker is secured by shrink material. The marker includes multiple layers. The layers have a thickness of about 0.005 inches or 0.001 inches or less. The fluoroscopic imaging enhancement material and MRI enhancement layer are provided in separate layers. The marker includes three or more layers. The marker includes 4 to 20 layers. The marker includes a drug layer. The marker has a first layer including a fluoroscopic imaging enhancement material and a second layer having an MRI enhancement material, and a third layer. The third layer is in contact with the body. The third layer is between the first and second layers. The third layer defines an exterior surface of the marker. The fluoroscopic imaging enhancement material and the MRI enhancement material are in separate layers and the MRI imaging enhancement material has a radiopacity of about 0.9, 0.5, 0.1 or less than the radiopacity of stainless steel. The MRI enhancement material has an atomic number of 40 or less. The marker includes a layer including MRI enhancement material, the layer having a thickness of about 1 micron or less.

Embodiments may include one or more of the following. The MRI enhancement material is present at 25%, 10%, 1% or 0.1% or less by weight of the fluoroscopic imaging enhancement material. The marker has a radiopacity of about 1.1, 2.0 or 3.5 times stainless steel. The marker has a MRI visibility about equal or greater than about 280 mg/ml gadodiamine in 5000 ml blood. The fluoroscopic imaging material has a density of about 9.9 g/cm$^3$ or 21 g/cm$^3$ or more. The fluoroscopic material is gold, platinum, tungsten, tantalum, rhenium, bismuth, silver, iridium and mixtures, compounds, complexes and mixtures thereof. The MRI material is ferromagnetic, paramagnetic or superparamagnetic. The MRI material has a magnetic susceptibility of about 500× 10$^{-6}$ Emu or greater. The MRI material is selected from nickel, iron, magnesium, cobalt and alloys, oxides and mixtures thereof. The MRI material is gadolinium, dysprosium, terbium and alloys and oxides thereof. The marker extends over at least 50% or 75% of the circumference of the body. The fluoroscopic imaging material and MRI material are arranged concentrically with respect to one another. The marker is noncircumferentially conducting. The polymer body is on a catheter. The catheter is formed entirely of polymer at the location where the marker is secured. The catheter is a balloon catheter. The device includes multiple markers secured to the polymer body at locations indicative of the location of a balloon carried by a balloon catheter. The polymer body is a guidewire. The guidewire is composed entirely of polymer at the location the marker is secured to the body. The polymer body is a stent. The marker is secured by a first layer including an imaging enhancement material on the medical device; and securing a second layer comprising an imaging enhancing material on the medical device, such that the first and second layers are concentric. The medical device, at the location of said securing has a radiopacity less than stainless steel. The medical device, at the location of said securing, is composed of substantially nonferromagnetic, paramagnetic or superparamagnetic material.

Embodiments may include one or more of the following. The fluoroscopic imaging enhancement material has a linear attenuation coefficient of about 25 cm$^{-1}$ or more at 100 KeV. The superparagmagnetic material is nanosized particles of nickel, iron, magnesium, cobalt, and alloys thereof. The fluoroscopic imaging enhancement material and/or the MRI enhancement material of the marking system is disposed within a matrix formed of a polymer or a ceramic.

Embodiments may include one or more of the following. The marker has a generally annular shape. The marker has a generally linear shape. The marking system includes multiple, particularly three or more layers that each have a thickness between about 0.00005 inches and about 0.005 inches. The marking system has five or more layers and one of the layers is a bonding layer and/or one of the layers can be a drug-delivery layer. The marking system is incorporated in a catheter, guidewire, medical coil, pacer lead, or stent. The marking system is incorporated in a medical device formed of a polymer body. The medical device is a polymer guidewire, stent, or coil.

Embodiments may include one or more of the following advantages. A marking system provides effective imaging of a common location by both MRI and fluoroscopic imaging. Materials particularly suited for MRI and materials particularly suited for fluoroscopic imaging are combined in multiple layers to provide mechanical, chemical, and imaging compatibility. The materials are provided in discrete, bonded layers, which can be arranged to enhance imaging characteristics, or combined with other materials to enhance bonding characteristics between layers or to a medical device, or to distribute forces such as compression or tension imposed on the member in use, e.g. in a flexible medical device such as a catheter. Imaging compatibility is enhanced by selecting the type and amount of the imaging materials. For example, a marker can combine a relatively large amount of fluoroscopic imaging enhancement material to enhance X-ray absorption and a relatively small amount of MRI enhancement material to provide magnetic perturbation of only the local environment. The location of the MRI enhancement material relative to the thickness of the marker can be selected to control the degree of magnetic perturbation. A marker can be easily and economically attached to a medical device, e.g. by crimping, melting, heat-shrinking or with adhesive. The marker can include many, e.g. 5 or more, layers and may be formed by co-extrusion.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a side view of catheter including a marking system.

FIG. 1B is an expanded view of a portion of FIG. 1A labeled A.

FIG. 6 is a side view of a guidewire.

Like reference symbols in the various drawings indicate like elements. All publications and patent documents referenced herein are incorporated herein by reference in their entirety.

DETAILED DESCRIPTION

Figure 2A:
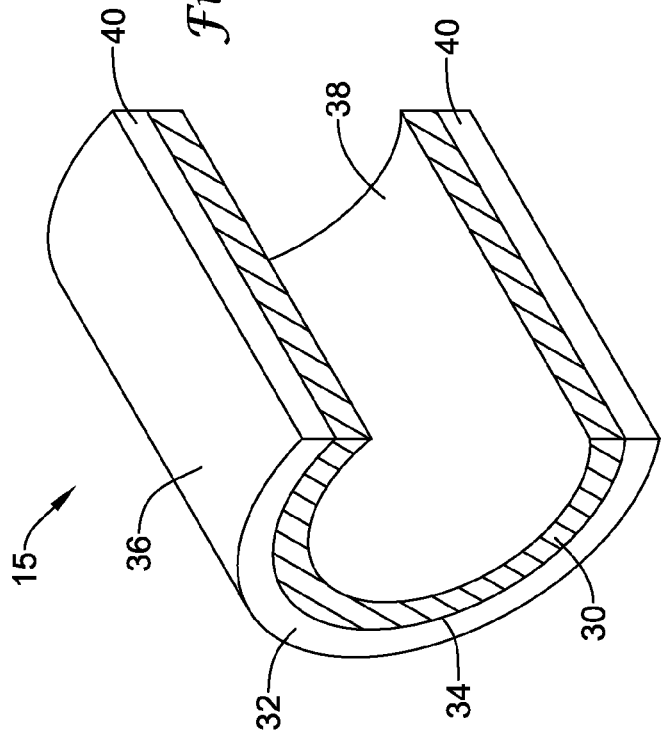
FIG. 2A is a perspective view of an embodiment of a marker.

Referring to FIGS. 1A and 1B, balloon catheter 2 includes a proximal connector section 4 and a catheter body 6 (the shaft) that carries an inflatable balloon 8 at its distal end. Balloon 8 includes an inflatable portion 19 and two sleeve portions 21 that are secured to catheter body 6. Connector section 4 has a connector 5 through which a guidewire may extend and a connector 7 through which fluid can be introduced to inflate balloon 8. Connectors 5, 7 communicate with lumens within catheter body 6 that direct the guidewire and inflation fluid along the length of the catheter. An inflation fluid lumen terminates in an opening 9 so that inflation fluid may be introduced into the interior of inflation portion 19 of balloon 8. A guidewire lumen 11 extends to the distal end of the catheter body 6. A particular balloon catheter is sized and constructed for use in the vasculature, e.g. the coronary arteries for angioplasty treatment, including stent delivery. Balloon catheters are described in Solar U.S. Pat. No. 4,976,690 and Sahatjian U.S. Pat. No. 5,270,086, the entire contents of which are hereby incorporated by reference.

Figure 2B:
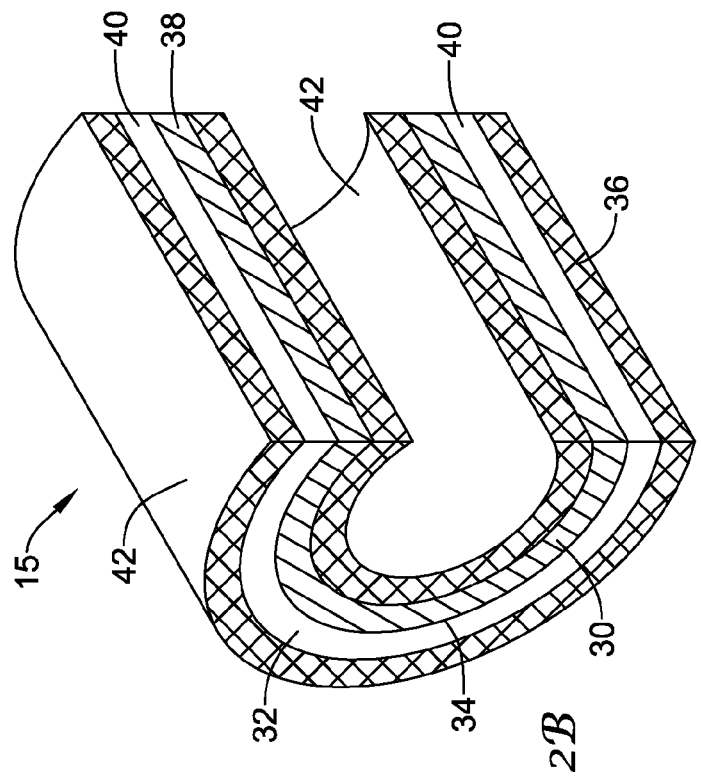
FIG. 2B is a perspective view of another embodiment of a marker.

Catheter 2 includes markers 15, 15' positioned along the catheter body at locations corresponding to the proximal and distal regions of the inflatable portion of the balloon 8. Referring to FIG. 2A, markers 15, 15' are C-shaped bands that include a first imaging layer 30, e.g. a radiopaque layer visible under fluoroscopy and a second imaging layer, e.g. an MRI visibility enhancement layer 32. Layers 30 and 32 are positioned concentrically to each other and are bonded at an interface 34 so that a common location can be imaged by both MRI and fluoroscopy. Referring to FIG. 2B, outer surfaces 36, 38, and 40 can be each provided with a layer 42 of biocompatible material, such as polymer, e.g. polyethylene, polyurethane, and/or can be provided with a coating of a therapeutic agent such as an antithrombogenic or antiproliferative agent. (Layer 42 can be provided on one or more of surfaces 36, 38, 40. In FIG. 2B, layer 42 is shown only on surfaces 36, 38.) While in FIG. 1B, the markers are located underneath balloon 8, the layer 42 is particularly useful in embodiments in which the marker is located in direct contact with body fluid, such as for example, proximal or distal to balloon 8, as illustrated in FIGS. 3A-3F.

Figure 3A:
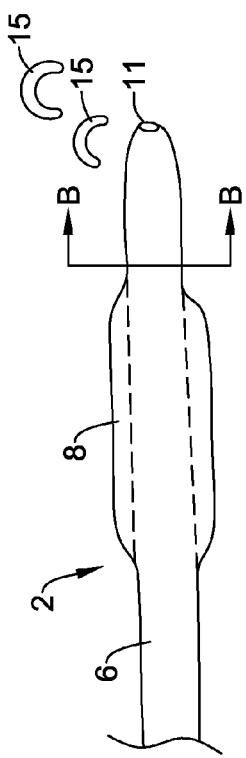
FIG. 3A is a side view of a catheter prior to attaching a marker.
Figure 3B:
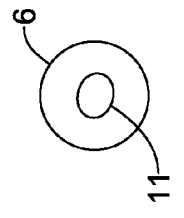
FIG. 3B is a cross-sectional view of the catheter taken along line B-B in FIG. 3A.
Figure 3C:
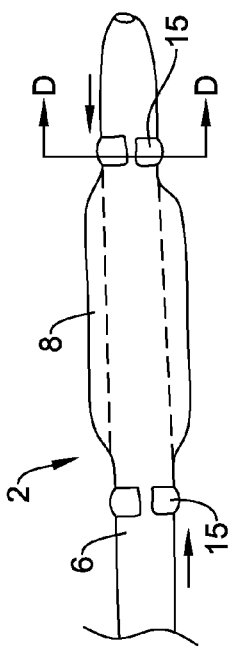
FIG. 3C is a side view of a catheter with two markers positioned on the catheter.
Figure 3D:
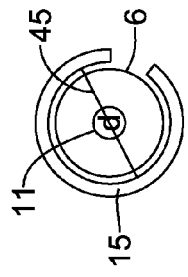
FIG. 3D is a cross-sectional view of the catheter taken along line D-D in FIG. 3C.

Referring to FIGS. 3A-3F, particularly FIGS. 3A and 3B, markers 15, 15' and the catheter body are manufactured as separate items, which are then assembled. Referring to FIGS. 3C and 3D, markers 15 are sized so that they can be slid (arrows) over the distal and proximal ends of the catheter body 6 and positioned adjacent the balloon 8. (Alternatively, both markers can be slid onto the catheter body from the same end of the catheter body if they are sized to slide over the balloon or if the balloon is attached after the markers are disposed on the body. The markers can also be disposed laterally over the body if the gap in the C-shaped band is sized to adapt to the catheter diameter).

Figure 3E:
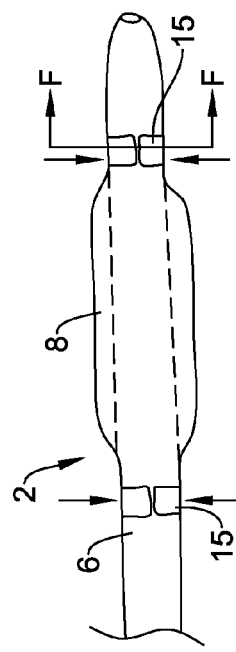
FIG. 3E is a side view of a catheter with the markers secured to the catheter.
Figure 3F:
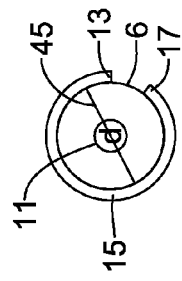
FIG. 3F is a cross-sectional view of the catheter taken along line F-F in FIG. 3D.

Referring to FIGS. 3E and 3F, the markers 15, 15' are secured to the catheter body. In embodiments, the marker is plastically crimped to reduce the inner diameter (d) 45 (arrow) so that it is friction fit onto the body. In embodiments the markers include a male connector at, for example, location 13 and a female connector at, for example, location 17 of the C-shaped band, such that after crimping a lock mechanism, such as a pin and hole or a dovetail connection, is made. Alternatively or in addition an adhesive, such as a biocompatible glue can be applied to secure a marker to the catheter body. In embodiments, a heat shrink material placed over the marker can be used to secure markers 15, 15' to catheter 2. In embodiments, the marker can be assembled as it is secured. For example, a first layer can be disposed on the catheter and a second layer, e.g. adhesive or heat shrink carrying imaging material is disposed over the first layer and secured to the catheter. In embodiments, markers can be secured within grooves cut into the catheter body. For example, laser ablation can be used to remove a circumferential strip from the outer surface of the polymer tube to form grooves, which are sized to a depth such that a marker fits into the groove and is flush with the catheter body outer surface. Excimer laser ablation can be performed utilizing a 248 nm laser with an energy density of about 500 mJ/cm$^2$.

The materials in the marker layers, as well as the number, order, and thickness of the layers are selected to provide desirable imaging and mechanical characteristics. For fluoroscopic visualization, the marker includes materials that are X ray absorbing in amounts sufficient to provide a desirable contrast. Materials that are highly X ray absorbing can be selected by their linear attenuation coefficient, atomic number, and/or density. Materials particularly suited for visualization under fluoroscopy have a linear attenuation coefficient of at least about 25 cm$^{-1}$ or more at 100 KeV (e.g., at least about 50 cm$^{-1}$, or more at 100 KeV, at least about 105 cm$^{-1}$, or more at 100 KeV). Materials that have an atomic number (elements) or an effective atomic number (weighted average of the atomic number of each of the elements that form a compound, mixture, or alloy) of about 40 or more and a density of about 9.9 grams/cm$^3$ or more (e.g., 21.45 grams/cm$^3$ or more) are particularly desirable. Examples of fluoroscopic imaging materials include gold, platinum, tungsten, tantalum, rhenium, bismuth, silver, iridium, and complexes, compounds and mixtures thereof. In embodiments, the marker has a radiopacity such that the marker is readily visible by fluoroscopy but does not appear so bright that detail in the image is disturbed. In embodiments, the marker itself, or the region of the medical device including the marker, has a radiopacity of about 1.1 to about 3.5 times that of 316L stainless steel. A technique for measuring radiopacity is described in ASTM F640. Radiopacity and radiopaque materials are also discussed in U.S. Pat. No. 5,725,570 issued to Heath and in U.S. Pat. No. 5,628,787 issued to Mayer, the entire disclosures of which are hereby incorporated by reference.

For MRI visualization, imaging is enhanced by materials that are themselves imagable by magnetic resonance effects or materials that modify the magnetic environment adjacent the marker to produce imaging effects of other materials, e.g. by modifying T1 and/or T2 of protons in tissue adjacent the marker. In embodiments, the MRI imaging materials are selected based on magnetic susceptibility. In embodiments, the magnetic susceptibility is e.g. about 500×10$^{-6}$ Emu or 600×10$^{-6}$ Emu or greater at room temperature. Suitable materials include ferromagnetics or paramagnetics, which modify the magnetic environment of adjacent body tissue. Examples of ferromagnetic materials include, for example, nickel, iron, magnesium, cobalt, and alloys and oxides of these materials. Examples of paramagnetic materials include gadolinium, dysprosium, terbium, and alloys and oxides thereof. A particular material is dysprosium oxide, a strong paramagnetic (590×10$^{-6}$ Emu). Examples of superparamagnetic materials include nanosized particles of nickel, iron, magnesium, cobalt and alloys and oxides thereof.

The amount and configuration of the MRI imaging material is also selected to provide desired imaging effects, e.g. such as high resolution imaging. For example, for ferromagnetic, paramagnetic, and superparamagnetic materials, which interfere with the local imaging, the volume or large particle size of interfering material is selected to avoid substantial image distortion image. Small particles (e.g., particles having a volume less than about 3×10$^{-6}$ mm$^3$) or thin layer (e.g., layers having a thickness less than about 0.3 µm) generate a small bright band (e.g. about 5 voxels or less) in the MRI at the location of the marker without distorting the entire image or interfering with the image visibility. Image visibility can be determined by comparison to an MRI contrast agent such as Omniscan (Gadodiamine, Nycomed). For example, a clear bright contrast is obtained when using 20 ml injection bolus for an adult (5000 ml blood). Omniscan contains 287 mg/ml Gadodiamide, a Gadolinium compound. Taking a voxel with sizes of 0.4 mm, one voxel has therefore a content of 0.064 cubic mm, which is equal to 0.064 microliter blood inside the blood vessel. A desirable visibility is 2 voxels or more radial visibility around the marker. In embodiments including a French 6 catheter, a marker having a 2 mm diameter and a length of 1 mm, one needs to brighten an annular space of 0.8 mm surrounding the marker (being 2 voxels). The total volume to be affected as such is 7 cubic millimeter, which equals 109 voxels. To obtain the same brightness around the marker, the marker includes a similar amount of gadolinium as being diluted in the blood within 109 voxels when Omniscan is being used. Therefore the amount of Gadolinium is greater than 8×10$^{-3}$ mg, i.e., 8×10$^{-3}$ mg=109 voxels×[0.064×10$^{-3}$ (ml/voxel)]×[20 ml/5000 ml]×287 [mg/ml]. Gd$_2$O$_3$ (molecular weight mainly due to gadolinium) has a density of 7100 kg/m$^3$. Thus, 1.13×10$^{-12}$ m$^3$ GdO is used to brighten a region of 2 voxels around a markerband in an MRI. This volume corresponds to a layer of 0.18 micrometer on the markerband. In particular embodiments, the type, amount, and/or configuration of MRI imaging materials is selected such that artifacts in the magnetic resonance image do not substantially effect the quality of the diagnostic information desired. A technique for measuring artifacts is described in ATSM F2119-01.

In embodiments, the marker does not create excessive movement, heating, induced current, or undesirable artifacts as described in "MRI Compatibility and Visibility Assessment of Implantable Medical Device" by Schueler et al., Journal of Magnetic Resonance Imaging, Vol 9, 1999, pages 596-603, the disclosure of which is hereby incorporated by reference.

In particular embodiments, a marker includes two different imaging enhancement materials, one for facilitating fluoroscopic imaging and one for enhancing MRI. The type, amount, and arrangement of the two materials in the marker can be selected to enhance imaging by both techniques while the material for enhancing one technique does not substantially degrade imaging by the other technique. The use of two different materials permits the imaging by both techniques to be optimized, thus reducing compromises in image quality created by a single material to provide imaging by both techniques. For example, the fluoroscopic imaging enhancement materials typically rely on absorption of X-ray radiation and are present in substantially greater amount than MRI enhancement material, which relies on interaction with applied magnetic fields. Using two enhancement materials, the relative amounts for both imaging techniques can be optimized so that the marker is clearly visible by both imaging techniques. For example, MRI imaging material may be 25% or less, 10%, 5% or 1% or less by weight of the fluoroscopic imaging material. In embodiments, the MRI enhancing material or layer does not substantially contribute to radiopacity. For example, the MRI enhancing material or layer has a radiopacity of about 0.9, 0.5, 0.1 or less than the radiopacity of 316L stainless steel per ASTM F640. In embodiments, the atomic number of the MRI enhancement is less than the atomic number of the fluoroscopic imaging enhancement material. For example, the MRI enhancement material can have an atomic number less than 40. In embodiments, the fluoroscopic visualization material is selected to minimize interference with MRI. For example, the fluoroscopic imaging material is non-paramagnetic.

The layers including MRI and fluoroscopic imaging materials can be formed entirely of the imaging materials or the imaging materials can be incorporated into a matrix material. The matrix material can be selected for its bonding properties. For example, the matrix material may be selected for its ability to bond to an adjacent layer or the body of a medical device. The matrix material can be selected for biocompatibility properties. The matrix material can also selected based on mechanical properties to complement, for example, the properties of the medical device. The matrix material can be, for example, a ceramic, polymer, or a metal. Suitable materials include metal oxides and metal nitrides. Examples are zirconium oxide and titanium oxide. A discussion of titanium oxide and other coatings is provided in U.S. Pat. No. 6,217,607 issued on Apr. 17, 2001, and U.S. patent application Ser. No. 09/740,570 filed on Dec. 18, 2000, the disclosure of each are hereby incorporated by reference. Suitable polymers include polyethylene, polyesters, polyamides, polyurethane, Pebax, Arnitel, Hytrel, polypropylene, polyolefins and polyimides.

In embodiments, the marker includes antithrombogenic, drug delivery, bonding, and/or compatibility layers. Suitable antithrombogenic layers include medical polymers such as styrene-isobutylene-styrene, polysaccharides, electroactive polymers, such as polypyrrole, metals such as stainless steel, or ceramics such as iridium-oxide. Suitable drug eluting layers include drug coatings or polymer coatings including drugs. Suitable drugs, particular for vascular applications include antithrombogenics or antiproliferatives. Other suitable drugs include antibiotic or antiviral compounds. Suitable drug-delivery polymers include biodegradable materials. Alternatively or additionally, the drug-delivery polymers may be, for example, homopolymers or copolymers, crosslinked or uncrosslinked, linear or branched, natural or synthetic, thermoplastic or thermosetting. Examples of drug-delivery polymers include the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, styrene polymers and copolymers such as polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS, see, e.g., U.S. Pat. No. 6,545,097), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephtalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and additional copolymers of the above.

Suitable bonding layers include polymers compatible with bonding to a medical device. For example, for melt bonding, the polymer may be the same as the polymer on the medical device to which the marker is to be attached. For adhesive bonding, the polymer may be compatible with a desired adhesive system or a heat shrink material. Suitable compatibility layers include polymers that are compatible with layers on either side of the compatible layer to avoid delamination. The number, thickness, and arrangement of the layers are selected to enhance performance.

In embodiments, the marker is generally arcuate with adjacent layers arranged concentrically. As illustrated above, the markers can be C-shaped. A C-shaped marker limits circumferential conduction so that electrical currents will not loop the marker band and produce artifacts. In other embodiments, the band is a circular band, an oval band, or other-shaped band, rather than C-shaped. In embodiments where the marker includes a looped band, the layers are prepared such that they do not form a continuous conducting circuit in a plane that is perpendicular to the longitudinal axis of the medical device. In other embodiments, the marker includes imagable material e.g. a linear strip or discrete pellets disposed within a plastic body. For example, the pellets include a core of one imaging material and a covering layer over the core including another imaging material. In embodiments, the marker can include projections or voids that mate with features on the medical device to discourage movement of the marker. For example, the marker can include projections that mate with openings on the medical device. In embodiments, the projections can be on an inward-facing surface and can penetrate into the medical device body, e.g. formed of polymer.

Figure 4:
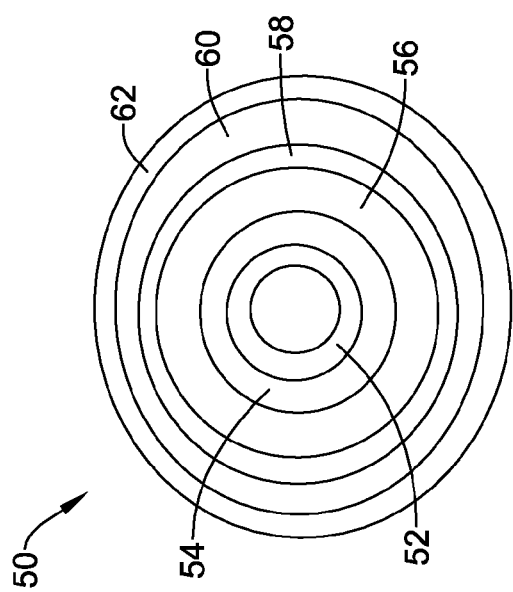
FIG. 4 is a cross-sectional view of an embodiment of a marker.

Referring to FIG. 4, a marker 50 including six layers is illustrated. The marker 50 includes a bonding layer 52, a compatibility layer 54, a first fluoroscopic imaging layer 56, an MRI layer 58, a second fluoroscopic imaging layer 60, and a drug eluting layer 62. The bonding layer is the inner most layer and selected to provide a firm bond to the catheter body. The compatibility layer 54 enhances bond strength between the bonding layer 52 and the first fluoroscopic imaging layer 56. The fluoroscopic imaging material is provided in multiple layers 56, 60 which are spaced radially within the marker. The fluoroscopic material, such as dense metals are typically relatively stiff. The flexibility of the marker is enhanced by using multiple layers of varying thickness. In addition, the stiffer layers can be located toward the inner diameter of the marker where the compression forces as the marker or catheter is flexed, are reduced.

The MRI layer 54 is provided between the fluoroscopic layers and may be relatively thin. The position of the MRI layer relative to adjacent tissue influences the magnitude of the magnetic perturbation on adjacent tissue and thus the MRI signal characteristics. For example, if the MRI material is positioned in layers spaced further from the tissue, the perturbation is generally less than the perturbation caused by locating the MRI material closer to adjacent tissue in outer layers of the marker.

Figure 5:
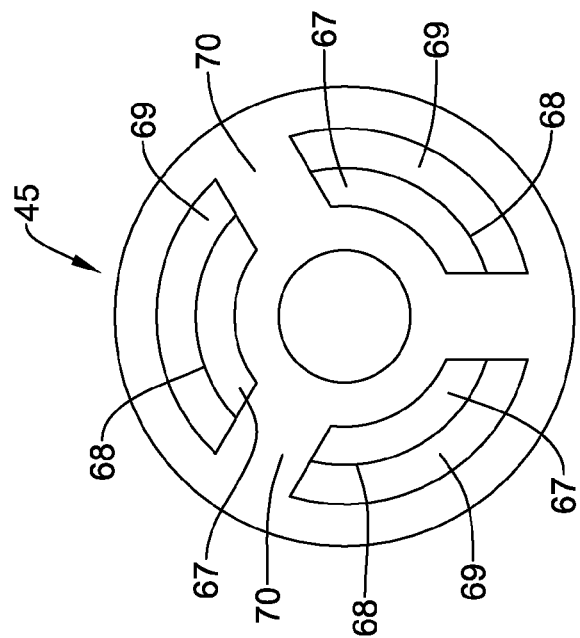
FIG. 5 is a cross-sectional view of another embodiment of the marker.

Referring to FIG. 5, marker 65 includes layers 67 and 69, which are concentric to each other and are bonded at interface 68. Layer 67 is made from a radiopaque material and layer 69 includes a MRI visibility enhancing material. Marker 65 also includes a non-conducting body material 70, such as a non-conductive polymer or ceramic. Layers 67 and 69 are embedded in material 70, such that the electrical conductivity of the marker is non-closed loop, such that the electrical conductivity of the marker along its circumference is interrupted by isolating parts. As such, no electrical currents can loop the marker band and additional RF artifacts in MRI are excluded.

Referring to FIG. 6, markers 15, 15', 15" are provided on a guidewire 80 positioned within a coronary artery. The guidewire 80 has a body 82 formed of a noncondutive material such as a polymer. The nonconductive guidewire body reduces the likelihood of heating or electrical stimulus of heart tissue caused by coupling the RF-energy during MRI. The markers 15, 15', 15" can be imaged by MRI and/or fluoroscopic imaging. Polymer guidewires are described in U.S. Pat. No. 6,436,056 the disclosure of which is hereby incorporated by reference. In other embodiments, the markers can be incorporated with other medical devices, such as an embolization coil, stent (e.g. a vascular, particularly coronary stent) or pacer lead. Stents, including balloon expandable and self-expanding stents, are further discussed in U.S. Pat. No. 5,725,570 issued to Heath. In particular embodiments, the markers are utilized with medical devices formed with a contiguous polymer body that is, e.g. extruded or molded. The polymer body can form an entire component of a medical device, e.g. a catheter shaft, or a portion of a component, e.g. a section of a shaft. In embodiments, the polymer body is not visible by X-ray or MRI visualization, In embodiments, the polymer body can be free of MRI and/or fluoroscopic imaging materials.

As discussed above, in embodiments, the markers include a multitude of layers, for example, 3 or more, e.g. 5 to 20 layers. Markers can be formed with multiple layers by molding, spraying, dipping, and extrusion. Metal layers can be formed by evaporative techniques or by metal injection molding (MIM) techniques. MIM is particularly suitable for complex stacking of many layers, because MIM is an additive process rather than subtractive, i.e., each layer is injection molded into a particular shape to form the marker. In addition, MIM can provide a non-smooth inner surface topography of the marker, such that, for example, spikes that can grip an underlying polymer medical device are formed along the inner surface of the marker. As a result, less clamping is required to attach the marker, as the spikes will prevent axial displacement. A particular technique for forming multiple layers of polymer materials is co-extrusion. A suitable technique for co-extrusion is described in U.S. patent application Ser. No. 09/798,749, filed Mar. 2, 2001 and in U.S. patent application Ser. No. 10/351,695, filed on Jan. 27, 2003, the disclosures of both are hereby incorporated by reference. In an additional example, the layers can be bonded together prior to attaching a marker to the medical device, or contain layers that can be joined such that they are concentric to each other after attachment to the medical device. For example, in embodiments, a layer of a radiopaque composition is attached to the medical device using a heat shrink material and a layer (which includes a MRI visibility enhancing composition) is glued to the heat shrink material, deposited onto the heat shrink material or incorporated within the heat shrink material. In embodiments, the thickness of the layers is between about 0.00005 inches to about 0.005 inches.

As another example, while the markers have been described as being attached to a medical device, the multilayer structure described above can also be used to form a medical device that is MRI and/or fluoroscopically imagable. An example is a multilayer polymer medical tube, including e.g. 3 to 20 layers or more, having MRI and/or fluoroscopic imaging materials therein. The tube can be formed by coextrusion as described in U.S. Ser. No. 09/798,749 and U.S. Ser. No. 10/351,695, previously incorporated by reference. The tube can be configured into a medical device such as a catheter body, a balloon or a graft or stent.

Suitable imaging equipment and clinical applications are described in Martin et al., Medica Murdi 46/3, November 2002, p. 28-34, the entire contents of which is hereby incorporated by reference.

Example 1

A marker is provided with a layer of gold or platinum having a thickness of about 0.002 inches. Bonded to the exterior circumference of the gold is a layer of a paramagnetic material such as gadolinium oxide or dysprosium oxide. The paramagnetic material has a thickness of about 0.0005 inches. The marker has an inner diameter of about 0.0795 inches and an outer diameter of about 0.0820 inches. The marker has a length of about 0.078 inches. The marker is made by forming a C-shaped ring of fluoroscopic imaging metal. The "C" shape having an opening of about 10 degrees, so as to retain at least a portion of the opening in the "C" after the marker has been reduced in diameter by crimping (i.e., the "C" shape remains after crimping). The MRI material is coated onto its surface by mixing 95% by weight of either gadolinium oxide or dysprosium oxide power with cyanoacrylate glue (Loctite 4061 available from Henkel Loctite Corp., Rocky Hill, Conn.) on the surface of the fluoroscopic layer. The marker can be slid over a Fr. 6 catheter body having a diameter of about 0.0787 inches and attached by crimping. To further secure the C-shaped marker in place, a PET shrink-tube (Advance Polymers, Inc., 13 Industrial Way, Salem, N.H. 03079) with a wall thickness of about 0.00015 inches and a length of about 0.015 inches.

Example 2

A marker is provided with an inner layer of polymer such as Nylon 12, which is loaded with 90 wt % of tungsten-oxide. The inner diameter of the marker is about 0.0535 inches and an outer diameter of the inner layer is 0.529 inches. Provided to the outer surface of the inner layer is a 0.001 inch layer of Nylon 12 loaded with 50 volume percent of 6 nanometer particles of superparamagnetic maghemite. The total assembly of the marker (i.e., the inner and outer layers) is made by a co-extrusion process. The marker can be slid over a Fr. 4 catheter body having a diameter of about 0.0525 inches and attached by either glue or by welding using a heatclamp.

Example 3

To provide a flush outer surface along the catheter body in the area of marker attachment (for example the marker described in Example 1), a round slit is ablated out of the catheter body having a total depth of about 0.0040 inches, which corresponds to the thickness of the marker plus the thickness of the heat shrink tube. The ablation is done using an excimer laser ablation process utilizing a 193 nanometer laser having an energy density of 500 mJ/cm2. The slit is made as wide as the marker (0.078 inches) and the length of the heat shrink tube is chosen to be the same as the marker.

While in embodiments, markers have been described as attached to medical devices having a polymer body (e.g., balloon catheter), markers can also be attached to devices having a body formed of any biocompatible material (e.g., polymer, metal, ceramic, biological tissue that is compatible with a patient's body). For example, the marker can be attached to a stent formed of metal or formed of a ceramic. Metal stents are described in U.S. Pat. No. 5,725,570 issued to heath and herein incorporated by reference. Ceramic stents are described in U.S. Pat. No. 6,589,286 issued to Litner and ceramic coated stents are described in U.S. Pat. No. 6,245,104 issued to Alt, all references herein incorporated by reference. In embodiments, the marker can be attached to a medical device formed of an autogeneous material and/or biologically derived materials. Examples of medical devices (e.g. implants) formed of autogeneous materials and/or biologically derived materials (tissues, proteins, cells, such as stem cells) include bone implants as described in "The Bare Bones of Bioactive Glass" published in *NASA Microgravity Research Highlights*, publication no. FS-2001-06-97-MSFC and "Direct Comparison of Human 'Local Bone' Versus Human Iliac Crest Bone for Spinal Fusion" by Lee et al. in *Orthopaedic Research Society 47th Annual Meeting*, Feb. 25-28, 2001, p. 0949, herein incorporated by reference.

All of the features disclosed herein may be combined in any combination. Each feature disclosed may be replaced by an alternative feature serving the same, equivalent, or similar purpose. Thus, unless expressly stated otherwise, each feature disclosed is only an example of a generic series of equivalent or similar features.

All publications, applications, and patents referred to in this application are herein incorporated by reference to the same extent as if each individual publication or patent was specifically and individually indicated to be incorporated by reference in their entirety.

Other embodiments are within the scope of the following claims.

What is claimed is:

1. A medical device, comprising: a biocompatible body, and an attachable marker band secured circumferentially to an outer surface of the biocompatible body, the marker including a fluoroscopic imaging enhancement material and an MRI enhancement material, wherein the fluoroscopic imaging enhancement material and MRI enhancement material are concentric with each other in separate and noncircumferentially contiguous layers.

2. The device of claim 1 wherein the biocompatible body comprises a polymer.

3. The device of claim 1, wherein the biocompatible body comprises a material selected from the group consisting of polymer, metal, ceramic, autogeneous materials, biologically derived materials and combinations thereof.

4. The device of claim 1 wherein the marker is secured by friction.

5. The device of claim 1 wherein the marker is secured by adhesive.

6. The device of claim 1 wherein the marker is secured by shrink material.

7. The device of claim 1 wherein the marker includes multiple layers.

8. The device of claim 7 wherein the layers have a thickness of about 0.005 inch or less.

9. The device of claim 1 wherein the marker includes three or more layers.

10. The device of claim 1 wherein the marker includes 4 to 20 layers.

11. The device of claim 1 wherein the marker includes a drug layer.

12. The device of claim 1 wherein the fluoroscopic imaging enhancement material is provided in a first layer and the MRI enhancement material is provided in a second layer, and a third layer.

13. The device of claim 12 wherein the third layer is in contact with said biocompatible body.

14. The device of claim 12 wherein said third layer is between the first and second layers.

15. The device of claim 12 wherein the third layer defines an exterior surface of the marker.

16. The device of claim 1 wherein the fluoroscopic imaging enhancement material and the MRI enhancement material are in separate layers and the MRI imaging enhancement material has a radiopacity of about 0.9 or less than the radiopacity of stainless steel.

17. The device of claim 16 wherein the MRI enhancement material has an atomic number of 40 or less.

18. The device of claim 16 wherein the layer including the MRI enhancement material has a thickness of about 1 micron or less.

19. The device of claim 1 wherein the MRI enhancement material is present at 25% or less by weight of the fluoroscopic imaging enhancement material.

20. The device of claim 1 wherein the marker has a radiopacity of about 1.1 times or more stainless steel.

21. The device of claim 1 wherein the marker has a MRI visibility about equal or greater than about 280 mg/ml gadodiamine in 5000 ml blood.

22. The device of claim 1 wherein the fluoroscopic imaging material has a density of about 9.9 g/cm$^3$ or more.

23. The device of claim 1 wherein the fluoroscopic material is selected from the list consisting of gold, platinum, tungsten, tantalum, rhenium, bismuth, silver, iridium and mixtures, compounds, complexes and mixtures thereof.

24. The device of claim 1 wherein the MRI enhancement material is ferromagnetic, paramagnetic or superparamagnetic.

25. The device of claim 1 wherein the MRI enhancement material has a magnetic susceptibility of about $500 \times 10^{-6}$ Emu or greater.

26. The device of claim 1 wherein the MRI enhancement material is selected from the list consisting of nickel, iron, magnesium, cobalt and alloys, oxides and mixtures thereof.

27. The device of claim 1 wherein the MRI enhancement material is selected from the list consisting of gadodiamine, dysprosium, terbium and alloys, oxides and mixtures thereof.

28. The device of claim 1 wherein the marker extends over at least 50% of the circumference of the body and the fluoroscopic imaging material and MRI enhancement material are arranged concentrically with respect to one another.

29. The device of claim 28 wherein the marker is non-circumferentially conducting.

30. The device of claim 29 wherein the marker extends over 70 to 85% of the circumference of the body.

31. The device of claim 1 wherein the biocompatible body is on a catheter.

32. The device of claim 31 wherein the catheter is formed entirely of polymer at the location where the marker is secured.

33. The device of claim 31 wherein the catheter is a balloon catheter.

34. The device of claim 33 including multiple marker bands secured to the biocompatible body at locations indicative of the location of a balloon carried by the balloon catheter.

35. The device of claim 1 wherein the biocompatible body is a guidewire.

36. The device of claim 35 wherein the guidewire is composed entirely of polymer at the location the marker is secured to the body.

37. The device of claim 1 wherein the biocompatible body is a stent.

38. A marking system for use with a medical device to mark a region thereof, comprising:
a marker band that is circumferentially attachable to an outer surface of the medical device, the marker band including a fluoroscopic imaging enhancement material and an MRI enhancement material;
wherein the fluoroscopic imaging enhancement material and the MRI enhancement material are provided in separate first and second layers, respectively,
wherein the first and second layers are concentric with each other and are bonded, and wherein each of the first and second layers is non-circumferentially contiguous.

39. The marking system of claim 38, wherein at least one of the fluoroscopic imaging enhancement material and MRI enhancement material is disposed within a matrix.

40. The marking system of claim 38, wherein the fluoroscopic imaging enhancement material and the MRI enhancement material are disposed within a matrix.

41. The marking system of claim 38, wherein the fluoroscopic imaging enhancement material comprises a pure metal.

42. The marking system of claim 38, wherein the MRI enhancement material is disposed within the matrix.

43. The marking system of claim 42, wherein the matrix is a polymer.

44. The marking system of claim 42, wherein the matrix is a ceramic.

45. The marking system of claim 38, wherein the marker band is noncircumferentially conducting.

46. The marking system of claim 38, wherein the device is selected from the group consisting of catheters, guidewires, medical coils, pacer leads, and vascular stents.

47. The marking system of claim 38 wherein the marker band has three or more concentric layers, and wherein at least one of the three or more layers comprises the fluoroscopic imaging enhancement material or the MRI enhancement material.

48. The marking system of claim 47, wherein the marker band comprises 4 to 20 layers.

49. The marking system of claim 47, wherein each of the layers has a thickness between about 0.00005 inches and about 0.005 inches.

50. The marking system of claim 47, wherein one of the layers comprises a bonding layer.

51. The marking system of claim 47, wherein one of the layers comprises a drug-delivery layer.

52. The marking system of claim 47 wherein the marker band includes an inward-facing projection.

53. A method of attaching a marker to a medical device, the method comprising:
positioning at least one marker band at a location along the medical device,
wherein a fluoroscopic enhancing material and a MRI enhancing material are provided on each marker in separate first and second layers, respectively,
wherein the first and second layers are concentric with each other and
wherein each layer is non-circumferentially contiguous; and
circumferentially securing the marker at the location.

54. The method of claim 53, wherein securing comprises crimping the marker onto the medical device.

55. The method of claim 53, wherein securing comprises adhering the marker onto the medical device.

56. The method of claim 55, wherein adhering comprises applying a glue.

57. The method of claim 55, wherein adhering comprises applying a heat shrink material.

58. The method of claim 53 wherein the medical device, at the location where the marker is secured, has a radiopacity less than stainless steel.

59. The method of claim 53 wherein the medical device, at the location where the marker is secured, is composed of substantially nonferromagnetic, paramagnetic or superparamagnetic material.

60. The medical device according to claim 1 wherein the marker is C-shaped.

61. The marking system according to claim 38 wherein the marker band is C-shaped.

62. The method according to claim 53 wherein the marker is C-shaped.

* * * * *